US007014621B2

(12) United States Patent  
Nelson

(10) Patent No.: US 7,014,621 B2  
(45) Date of Patent: Mar. 21, 2006

(54) ANKLE BRACE

(75) Inventor: Ronald E. Nelson, Cambridge, MN (US)

(73) Assignee: Mueller Sports Medicine, Inc., Prairie du Sac, WI (US)

( * ) Notice: Subject to any disclaimer, the term of this patent is extended or adjusted under 35 U.S.C. 154(b) by 367 days.

(21) Appl. No.: 10/313,273

(22) Filed: Dec. 6, 2002

(65) Prior Publication Data

US 2004/0111049 A1  Jun. 10, 2004

(51) Int. Cl.  
*A61F 5/00* (2006.01)  
*A61F 13/00* (2006.01)

(52) U.S. Cl. ...................................... 602/27
(58) Field of Classification Search .............. 602/65, 602/61, 60, 27, 23, 5, 62; 128/882  
See application file for complete search history.

(56) References Cited

U.S. PATENT DOCUMENTS

| | | |
|---|---|---|
| 325,280 A | 9/1885 | Smadbeck et al. |
| 332,727 A | 12/1885 | McEwen |
| 363,516 A | 5/1887 | Hackey |
| 605,299 A | 6/1898 | Perrottet |
| 765,024 A | 7/1904 | Lueck |
| 832,613 A | 10/1906 | Krieger |
| 851,950 A | 4/1907 | LeMat |
| 929,179 A | 7/1909 | Wood |
| 921,563 A | 9/1909 | Quenzer |
| 1,037,441 A | 9/1912 | Collis |
| 1,081,366 A | 12/1913 | Collis |
| 1,084,197 A | 1/1914 | Collis |
| 1,231,332 A | 6/1917 | Collis |
| 1,717,609 A | 6/1929 | Ludwig |
| 2,096,677 A | 10/1937 | Fassett |
| 2,994,322 A | 8/1961 | Cullen et al. |
| 3,028,861 A * | 4/1962 | Shapiro ........................ 602/65 |
| 3,073,305 A | 1/1963 | Biggs, Jr. et al. |
| 3,298,365 A | 1/1967 | Lewis |
| 3,323,232 A | 6/1967 | Danowsky |
| 3,327,410 A | 6/1967 | Park, Sr. et al. |
| 3,674,023 A * | 7/1972 | Mann .......................... 602/65 |
| 3,970,083 A | 7/1976 | Carrigan |
| 4,187,844 A | 2/1980 | Caprio, Jr. |
| 4,237,874 A | 12/1980 | Nelson |
| 4,527,556 A * | 7/1985 | Nelson ......................... 602/27 |
| 4,621,648 A * | 11/1986 | Ivany .......................... 602/27 |
| 4,727,863 A * | 3/1988 | Nelson ......................... 602/27 |
| 4,825,856 A | 5/1989 | Nelson |
| 4,998,537 A * | 3/1991 | Rau ............................. 602/27 |
| 5,000,195 A * | 3/1991 | Neal ............................ 602/27 |
| 5,007,417 A | 4/1991 | Bender |
| 5,109,613 A | 5/1992 | Van Dyke |

(Continued)

*Primary Examiner*—Danton D. DeMille  
*Assistant Examiner*—Huong Q. Pham  
(74) *Attorney, Agent, or Firm*—Foley & Lardner LLP

(57) ABSTRACT

An ankle brace comprising a base of flexible material shaped to wrap around the sides of a foot and ankle and underneath a portion of the foot, with a support strap for protecting the anterior talofibular ligament. The two ends of the support strap are fixed to the base at or near the forward edges of the base. The strap is not otherwise fixed to the base underneath the sole of the foot, allowing the strap to move freely under the foot to conform to the particular size and shape of the foot of a particular wearer. The ankle brace features a symmetric construction which allows the ankle brace to be worn on either the left or the right foot, simplifying manufacturing and inventory management.

15 Claims, 6 Drawing Sheets

U.S. PATENT DOCUMENTS

| | | |
|---|---|---|
| 5,135,473 A | 8/1992 | Epler et al. |
| 5,139,479 A * | 8/1992 | Peters .................. 602/27 |
| 5,242,379 A | 9/1993 | Harris et al. |
| 5,330,419 A * | 7/1994 | Toronto et al. .......... 602/27 |
| 5,425,701 A | 6/1995 | Oster et al. |
| 5,472,414 A | 12/1995 | Detty |
| 5,620,413 A | 4/1997 | Olson |
| 5,678,330 A | 10/1997 | Van Dyke et al. |
| 5,681,271 A * | 10/1997 | Nelson .................. 602/27 |
| 5,741,222 A * | 4/1998 | Fiore .................... 602/27 |
| D394,112 S | 5/1998 | Duback et al. |
| 5,795,316 A | 8/1998 | Gaylord |
| 6,022,332 A * | 2/2000 | Nelson .................. 602/27 |
| 6,652,474 B1 * | 11/2003 | Quinn et al. ............ 602/21 |

\* cited by examiner

ANKLE BRACE

FIELD OF THE INVENTION

This invention relates generally to the field of articles worn by persons to reduce the likelihood, severity, or exacerbation of injury to the body, and more specifically to the field of braces worn on the ankle.

BACKGROUND OF THE INVENTION

The ankle joint is one of the most frequently used joints in the body, as it is required for any activity that involves walking or running. The ankle joint connects the lower leg and the foot of a person, providing a pivot point that allows the foot to rotate relative to the lower leg. Together the lower leg, ankle joint, and foot make up a complex system that must be sturdy yet flexible in order to bear a person's weight while providing freedom of movement.

During ambulation, and especially during strenuous sports such as football, basketball, tennis, or soccer, quick changes in direction or uneven playing surfaces can cause the ankle to move beyond its normal range of motion, resulting in a sprained ankle. A sprained ankle may be painful, and can make sports less enjoyable, reduce athletic performance, and adversely affect day to day activities. Further, once an ankle joint has been injured, the injury is more likely to recur. For these reasons, there has long been motivation to find ways to protect the ankle without restricting freedom of motion, to prevent injuries and to protect the ankle during recovery from a previous injury.

The ankle joint itself is comprised of a bone structure held together by ligaments. The bone structure of the ankle consists of seven tarsal bones, including the talus, calcaneus (heel bone), and navicular bones. The talus is the bone which lies adjacent to the lower ends of the tibia and fibula (the two lower leg bones).

A single triangular shaped ligament, the deltoid ligament, holds together the medial (inside) portion of the ankle joint, joining the tibia, talus, calcaneus, and navicular bones. Because of its size, the deltoid ligament is strong and relatively resistant to sprain injuries.

Four major ligaments, named for the bones they join together and their relative positions, hold together the lateral (outside) portion of the ankle joint. The anterior inferior tibiofibular ligament, located at the top of the ankle joint, joins the tibia and fibula. The anterior and posterior talofibular ligaments, located at the front and rear of the ankle joint respectively, join the talus and the fibula. The calcaneofibular ligament, located at the rear of the ankle joint, joins the calcaneus to the fibula. Most ankle sprains involve these ligaments on the lateral portion of the ankle joint.

The ligaments and bone structure which comprise the ankle joint determine the four basic ways that the foot can move relative to the lower leg. Dorsiflexion is when the toes are drawn toward the tibia (shin), as would occur when leaning forward. Plantar flexion is when the toes are pointed away from the tibia, as would occur when standing on tiptoes. Inversion is when the foot turns inwards, and eversion is when the foot rotates outwards.

Sprains may occur in any ligament in the ankle, but most sprains involve two particular ligaments on the outside of the ankle, the anterior talofibular ligament, and to a lesser extent, the calcaneofibular ligament. When an ankle sprain occurs, the anterior talofibular ligament is usually the first to be injured, followed by injury to the calcaneofibular ligament. For this reason, a sprained ankle usually involves injury to the anterior talofibular ligament or to both the anterior talofibular and the calcaneofibular ligaments, but a sprained ankle usually does not involve injury to the calcaneofibular ligament alone.

Many ankle sprains are the result of inversion, where the foot is rotated inward, which stretches the anterior talofibular ligament beyond its elastic limit. Injury to the anterior talofibular ligament is especially likely when the foot is plantar flexed and then undergoes forcible inversion. When the foot is at maximum plantar flexion, when the toes are pointed downward as far as possible, the anterior talofibular ligament is pulled taut. When the anterior talofibular ligament is taut, that ligament cannot stretch any further and any subsequent forcible inversion may cause that ligament to be strained, or partially or completely torn. Such forcible inversion might occur, for example, when an athlete jumps in the air and then lands on their own inverted foot or on an uneven surface, such as a hole, another player, or some other obstacle.

Ankle braces have been used for many years, in a variety of specific embodiments directed to particular applications, including protection of the anterior talofibular ligament. However, prior ankle braces designed to protect the anterior talofibular ligament have been made to fit either the right foot or the left foot, but not both. Thus, an ankle brace designed to protect the anterior talofibular ligament which could be worn on either the left or right foot would be desirable, to simplify inventory management and reduce costs.

SUMMARY OF THE INVENTION

The present invention features an ankle brace comprising a base of flexible material shaped to wrap around the sides of a foot and ankle and underneath a portion of the foot, with a support strap for protecting the anterior talofibular ligament. The two ends of the support strap are fixed to the base at or near the forward edges of the base, and the support strap is not otherwise fixed to the base.

An ankle brace according to the invention features a symmetric construction such that the ankle brace may be worn on either the left or the right foot. This feature reduces the number of different products which must be manufactured and maintained in inventory, compared to other ankle braces which can be worn on only the left or the right foot.

An ankle brace according to the present invention features an anterior talofibular ligament support strap which is not secured to the base of the brace beneath the foot. This feature allows the strap to move freely under the foot, so that the support strap can conform to the particular size and shape of the foot of a particular wearer. This feature provides a better fit to a particular wearer, compared to other ankle braces which include an anterior talofibular ligament support strap which is secured to the base of the brace beneath the sole of the foot.

Further objects, features, and advantages of the invention will be apparent from the following detailed description when taken in conjunction with the accompanying drawings.

DETAILED DESCRIPTION OF THE INVENTION

Figure 1:
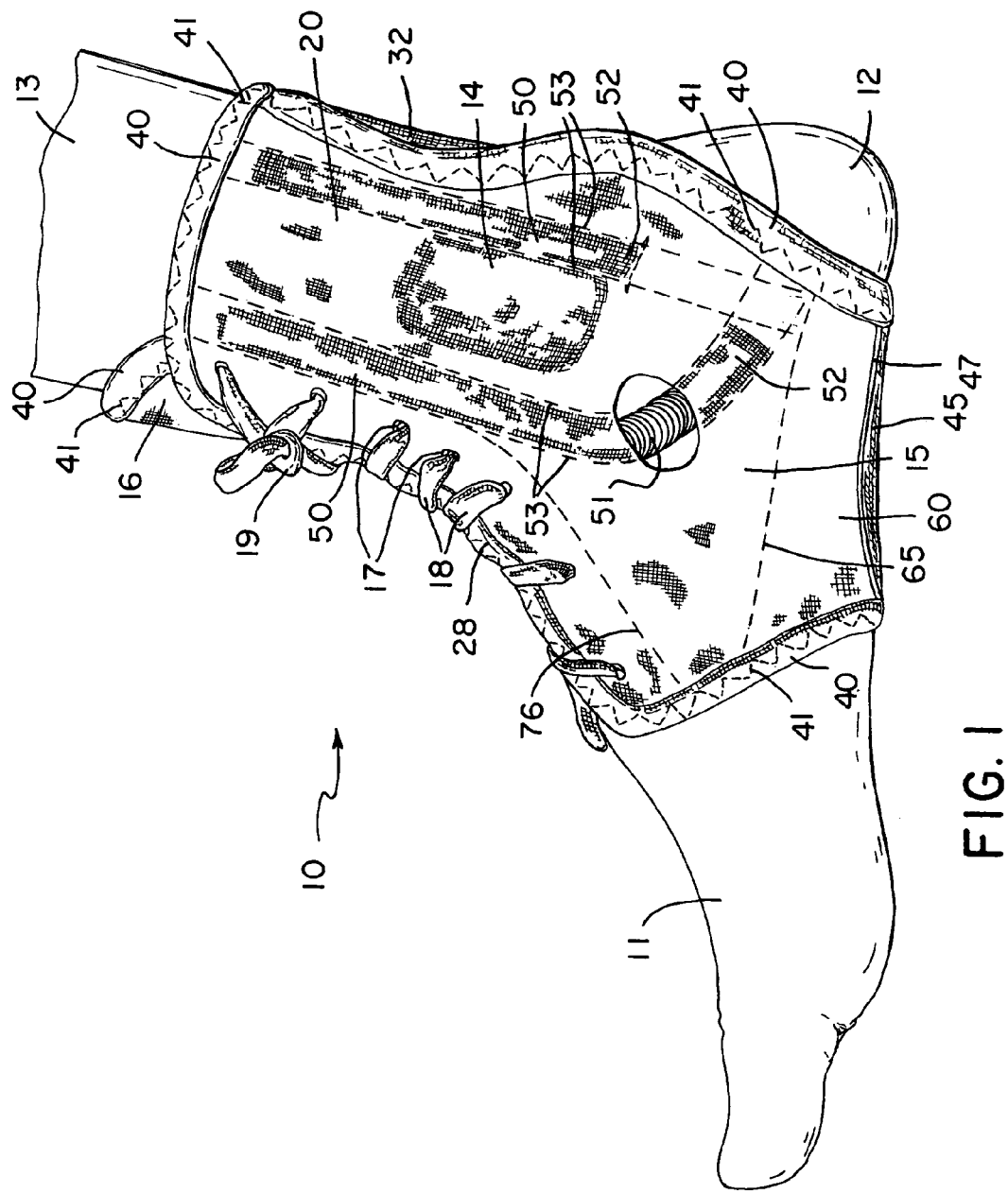
FIG. 1 is a side view of an ankle brace according to the invention installed on a foot.

With reference to the drawings, FIG. 1 is a side view of a preferred embodiment of an ankle brace in accordance with the invention, indicated generally at 10 in FIG. 1. The foot has a toe region 11 that extends out from an opening in the front of the ankle brace 10, and a heel region 12 that extends out from a opening in the rear of the ankle brace. The lower leg 13 of the person extends out from an opening at the top of the ankle brace. The brace 10 generally surrounds the ankle 14 of the person.

The ankle brace 10 is comprised of a base, indicated generally at 15, and a tongue 16, which are shaped generally to wrap about the foot and ankle of a person. The base 15 of the ankle brace 10 may be fastened about the foot using a plurality of eyelets 17 and a shoelace 18 tied in a knot 19. Although eyelets 17 and shoelace 18 are used in the preferred embodiment, other means such as straps or hook and loop material of the type that adheres when pressed together may be used.

Figure 2:
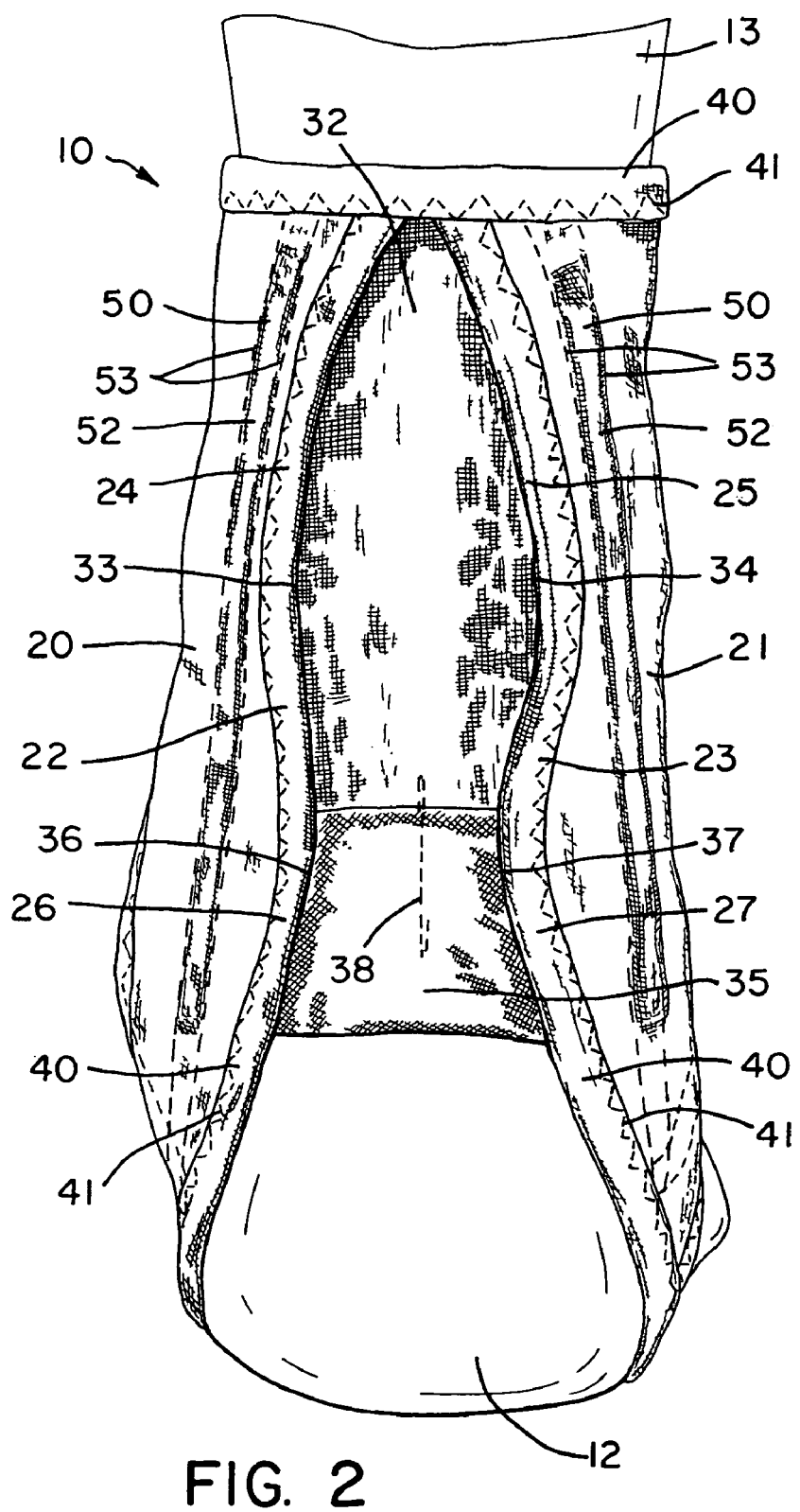
FIG. 2 is a rear view of an ankle brace according to the invention installed on a foot.

As best shown in FIG. 2, the base 15 of the ankle brace 10 has a first side 20 and a second side 21. The first side 20 of the base 15 has a rear edge 22, and this rear edge 22 has an upper portion 24 and a middle portion 26. The second side 21 of the base has a rear edge 23, and this rear edge 23 has an upper portion 25 and a middle portion 27.

Figure 4:
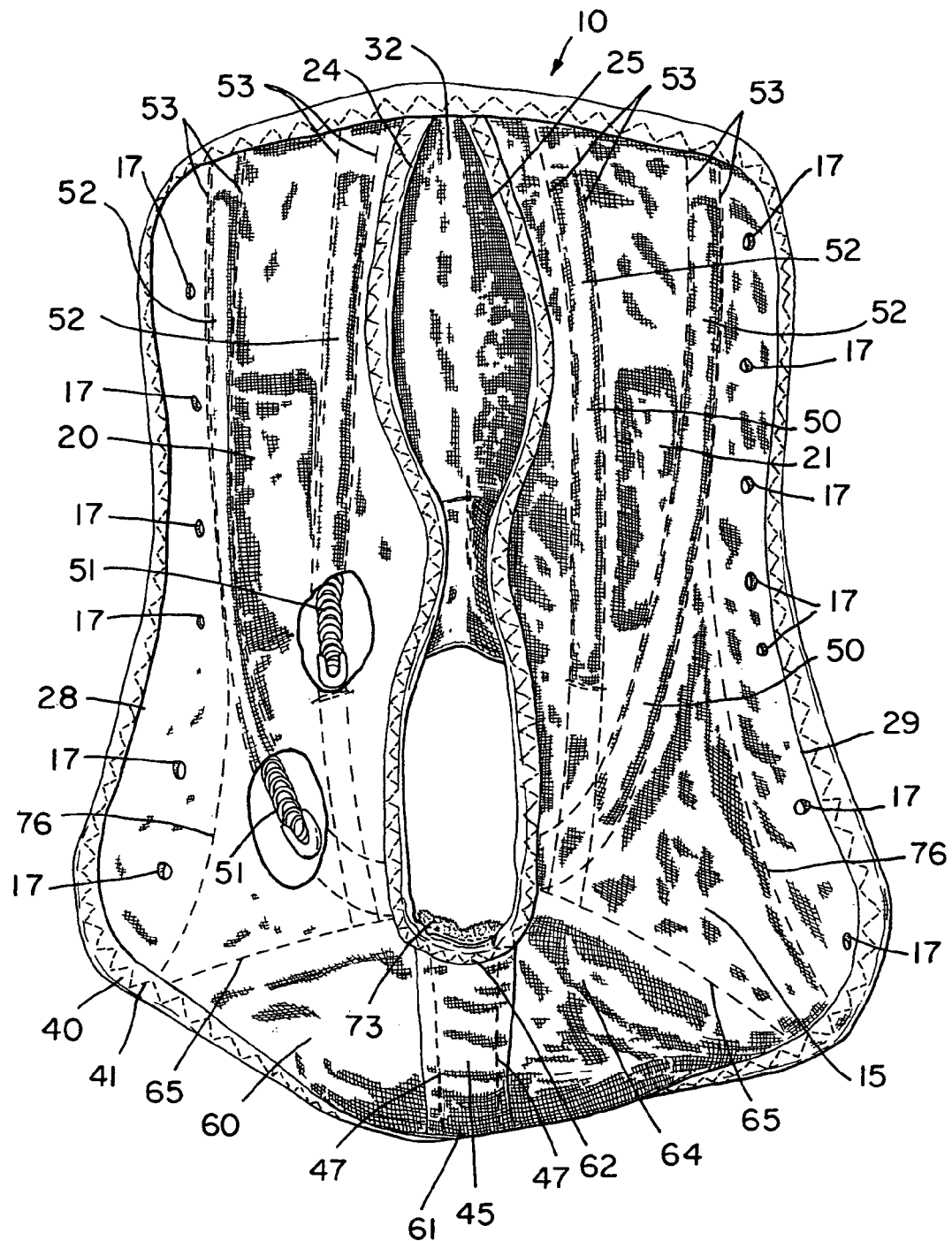
FIG. 4 is a rear view of an ankle brace according to the invention laid out flat, with the tongue and laces removed to show the internal construction.

As best shown in FIG. 4, the first side 20 of the base 15 has a forward edge 28, and the second side 21 of the base 15 has a forward edge 29. Eyelets 17 may be arranged along these forward edges. The shoelace 18 may be passed through the eyelets 17, placed under tension, and tied into a knot 27, in order to draw the first side forward edge 28 and the second side forward edge 29 together. The spacing of the eyelets 17 may be varied so that the tension of the ankle brace is greatest in the vicinity of the ankle, although this is not required.

Figure 3:
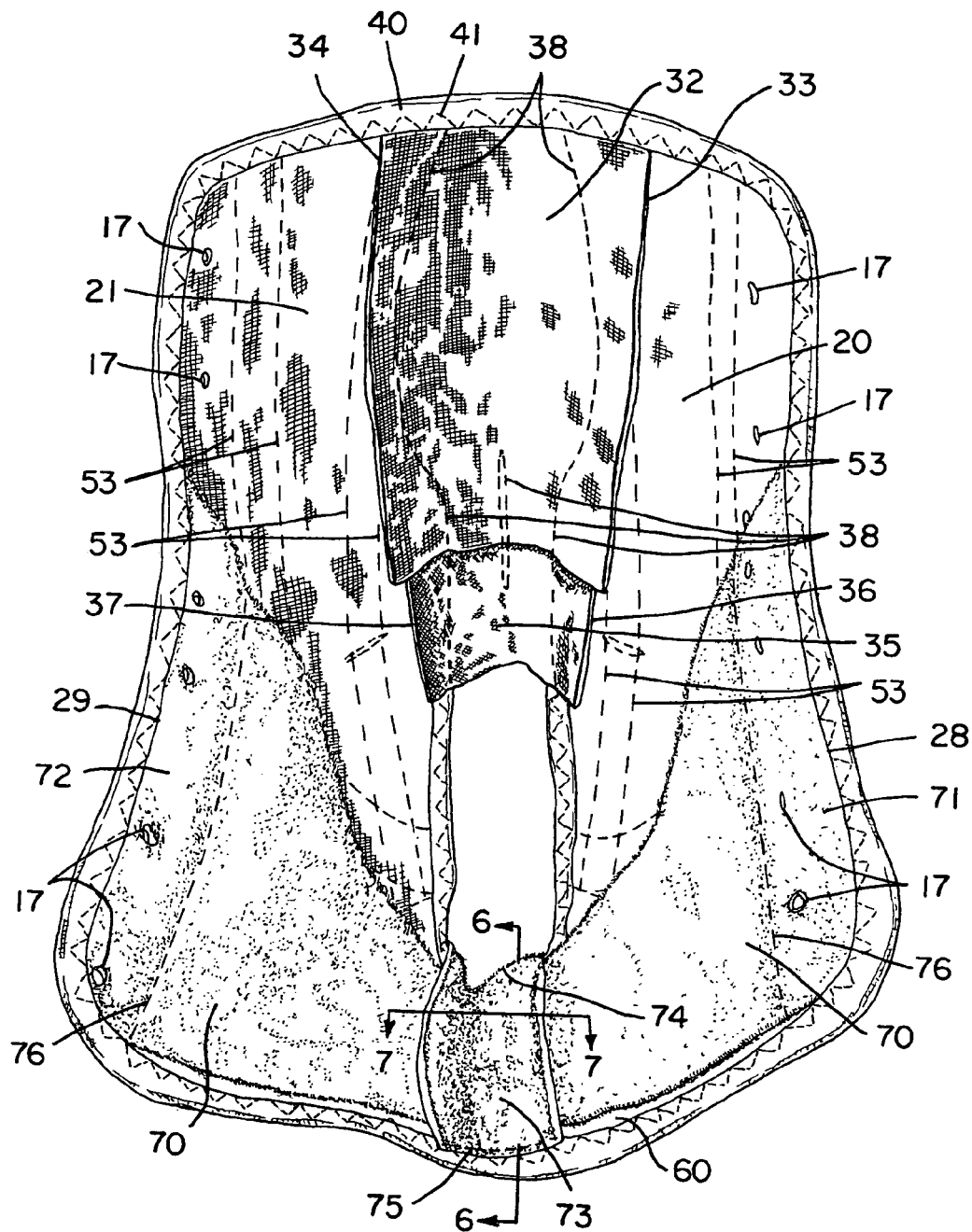
FIG. 3 is a front view of an ankle brace according to the invention laid out flat, with the tongue and laces removed to show the internal construction.

As best shown in FIGS. 2 and 3, the ankle brace preferably has an upper rear panel 32 having a first end 33 and a second end 34. The first end 33 and the second end 34 of the upper rear panel 32 are attached, for example using stitching 38, to the upper portions 24 and 25, respectively, of the rear edges of the first and second sides of the base. The upper rear panel 32 is preferably formed of elastic sheet material which stretches in both horizontal and vertical directions, although this is not required.

As best shown in FIGS. 2 and 3, the ankle brace preferably has a middle rear panel 35 having a first end 36 and a second end 37. The first end 36 and the second end 37 of the middle rear panel 35 are attached, for example using stitching 38, to the middle portions 26 and 27, respectively, of the rear edges of the first and second sides of the base. The middle rear panel 35 is preferably formed of directionally elastic sheet material which stretches in the horizontal direction but is relatively inelastic in the vertical direction, although this is not required. The upper rear panel 32 and the middle rear panel 35 may be secured to each other, for example using stitching 38, although this is not required.

As perhaps best shown in FIGS. 3 and 4, the first side 20 and the second side 21 of the base 15 are generally symmetric, such that the ankle brace 10 can be worn on either the left or right foot. Edge binding 40 may be secured, preferably using stitching 41, to cover the edges of the base 17 and the tongue 18, although this is not necessary.

Figure 6:
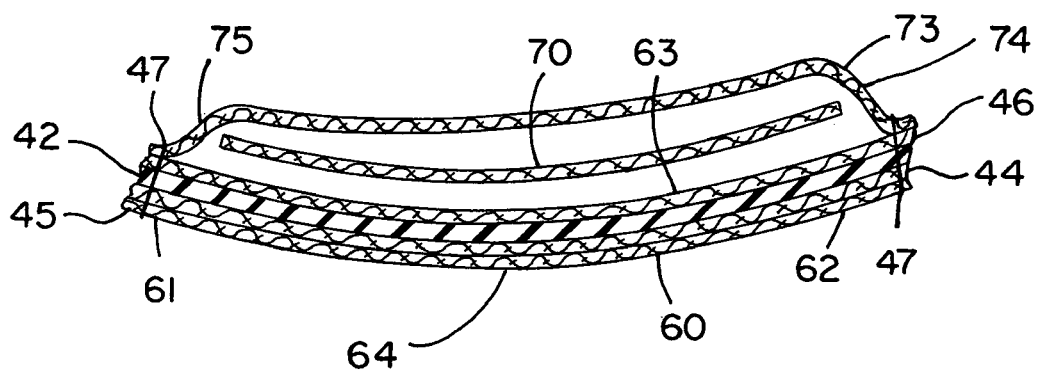
FIG. 6 is a cross-sectional view of the ankle brace of FIG. 3 taken along the line 6—6 thereof.
Figure 7:
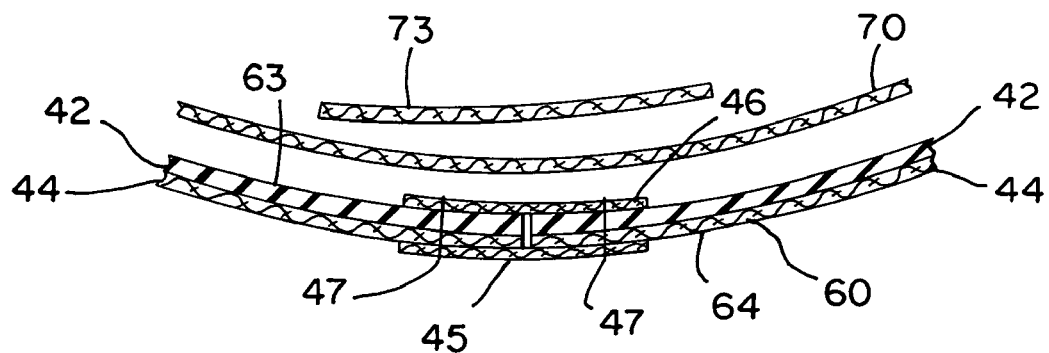
FIG. 7 is a cross-sectional view of the ankle brace of FIG. 3 taken along the line 7—7 thereof.

Although the first side 25 and second side 26 of the base 17 may be formed of a single layer of sheet material, they are preferably formed of multiple layers of sheet materials which are secured together, for example using stitches 41, although this is not required. As illustrated in FIGS. 6 and 7, an inside layer 42 and an outside layer 44 may be provided. The inside layer 42 may be chosen to have a soft surface since it may be in contact with the skin of the wearer. The outer layer material 44 may be chosen to be resistant to tearing, stains, and moisture, since it forms the outside surface of the ankle brace. Some portions of the base of the brace may also include a center layer (not shown) which may be chosen to be relatively rigid to provide structural integrity to those portions of the base of the ankle brace, although this is not required.

Although the base 15 may be made as a single piece, in a preferred embodiment the first side 20 and the second side 21 of the base 15 are made as separate pieces. In a preferred embodiment, an outside bottom edge attachment member 45 and an inside bottom edge attachment member 46 (shown in FIGS. 7 and 8) are provided to join the first side 20 and the second side 21 of the base 15, preferably using stitching 47.

Figure 8:
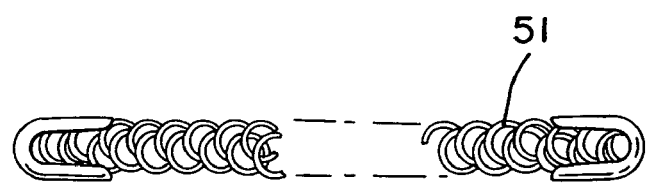
FIG. 8 is a side view of a resilient stay member made of flattened springs.

One or more resilient support means 50 may be provided on each side of the base of the brace, although this is not required. As best shown in FIG. 4, the resilient support means 50 are preferably comprised of a resilient stay member 51 located in an elongate pocket 52 formed between the outside layer 44 and the inside layer 42 of the base 15, preferably by stitching 53. Alternatively, if a center layer is provided, the elongate pocket 52 may be formed between the outside layer 44 and the center layer, or between the inside layer 42 and the center layer. The resilient stay member 51 may be formed of a pair of interleaved helical springs made of stainless steel that have been flattened, as shown in FIG. 8, or other flexible material of conventional construction commonly used in various types of braces.

In a preferred embodiment, two elongate pockets 52, each containing a resilient stay member 51, are located on each side of the brace, for a total of four resilient support means 50. As best shown in FIG. 1, a preferred embodiment includes one resilient support means 50 located behind the ankle, approximately vertical in orientation and roughly parallel to the rear edge of the base, and a second resilient support means 50 located forward of the ankle, running approximately vertically from a point above the ankle and then curving below the ankle.

FIGS. 3–7 best illustrate the construction of the sole portion 60 of the base of a preferred embodiment of an ankle brace according to the invention. As best shown in FIG. 4, the sole portion 60 corresponds generally to the area of the base bounded by forward edge 61, rear edge 62, and stitches 65 on each side of the base. The sole portion 60 has an inside surface 63 and an outside surface 64.

Figure 5:
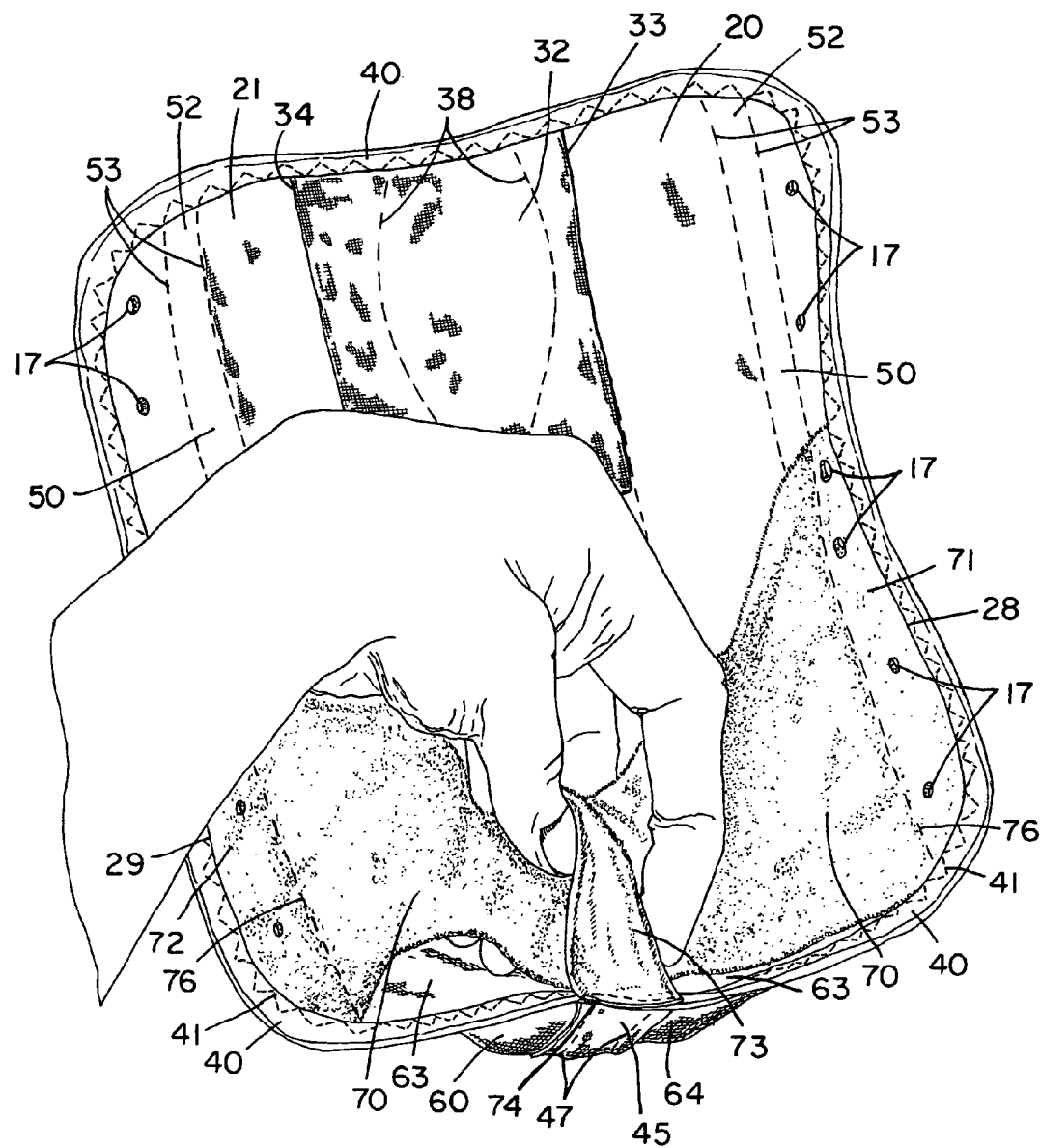
FIG. 5 is a front view of an ankle brace according to the invention, with the tongue and laces removed to show the internal construction.

As best shown in FIGS. 3 and 5, an ankle brace according to the invention includes a support strap 70 having a first end 71 and a second end 72. The first end 71 of the support strap 70 may be attached near the forward edge 28 of the first side 20 of the base 15, and the second end 72 of the support strap 70 may be attached near the forward edge 29 of the second side 21 of the base 15, preferably using stitches 76. In addition to or instead of stitches 76, the first end 71 of the support strap 70 may also be attached to the forward edge 28 of the first side 20 of the base 15, and the second end 72 of the support strap 70 may also be attached to the forward edge 29 of the second side 21 of the base 15 using stitches 41 which are used to secure the edge binding 40 to the edges of the base, although this is not required. In a preferred embodiment, the support strap 70 is unconnected to the base 15 at any point within the sole portion 60 of the base 15.

As best shown in FIGS. 3, 5, 6 and 7, an elongate sole strap 73, having a first end 74 and a second end 75, may be provided, although this is not required. The elongate sole strap 73 may be made of any sheet material having an appropriate strength and texture. The first end 74 of the elongate sole strap 73 may be attached to the forward edge 61 of the sole portion 60 of the base 15, and the second end 75 of the elongate sole strap 73 may be attached to the rear edge 62 of the sole portion 60 of the base 15, preferably using stitches 47. The elongate sole strap 73 is preferably otherwise unconnected to the base 15.

Thus it can be seen that the present invention provides an ankle brace which can be worn on either the left or right foot, and which is self-adjusting to fit the particular size and shape of the foot of the wearer. While the foregoing description contains many specificities, these should not be construed as limitations on the scope of the invention, but rather as an exemplification of one or more preferred embodiments thereof. Many other variations are possible.

For example, although a preferred embodiment of an ankle brace according to the invention includes a support strap with ends secured along a line near the forward edges of the sides of the base 15 using stitches 76, the ends of the support strap may be attached to other points at or near the forward edges of the sides of the base. Instead of using stitches, other means could be used to secure the ends of the support strap, such as glue, thermal bonding, or other means known in the art.

Instead of permanently securing the ends of the support strap, detachable attachment means such as hook and loop material of the type which adheres when pressed together could be provided on the support strap and along the inside of the base, to allow the support strap to be detachably attached to the base. Instead of or in addition to hook and loop material, the ends of the support strap could be provided with holes at a plurality of points near the ends of the support strap, and the shoelace 18 could be passed through a selected set of those holes in the support strap and through the eyelets 17.

There may be more than one elongated side pocket 72 containing a resilient stay member 74 on each side, and the elongated side pocket 72 may be openable at one end to allow removal of the resilient stay member or replacement of the resilient stay member with a different resilient stay member having different resiliency to adjust the amount of support provided.

Although shoelace and eyelets are used in a preferred embodiment to fasten the ankle brace around the foot and ankle. This could be done in other ways. Straps bearing hook and loop material of the type that adheres when pressed together could be used, with or without reversing loops, instead of or in combination with shoelace and eyelets. A greater or lesser number of straps, or eyelets could be used. An adjustable size closure assembly could be used, for example as set forth in U.S. Pat. No. 5,814,002, instead of or in combination with straps bearing hook and loop material, or shoelace and eyelets.

It is understood that the invention is not confined to the embodiments set forth herein as illustrative, but embraces all such forms thereof as come within the scope of the following claims.

What is claimed is:

1. An ankle brace, comprising:
   (a) a base of flexible material shaped to wrap around the sides of a foot and ankle and underneath a portion of the foot, the base having first and second sides, the first and second sides each having a forward edge; and
   (b) a support strap having a first end fixed to the base adjacent to the forward edge of the first side of the base and a second end fixed to the base adjacent to the forward edge of the second side of the base, wherein the support strap is not otherwise fixed to the base;
   wherein the first and second sides of the base each have a rear edge and the rear edges of the first and second sides each have an upper portion and a middle portion, and further comprising an upper rear panel having a first end fixed to the upper portion of the rear edge of the first side of the base and a second end fixed to the upper portion of the rear edge of the second side of the base; and
   further comprising a middle rear panel having a first end fixed to the middle portion of the rear edge of the first side of the base and a second end fixed to the middle portion of the rear edge of the second side of the base;
   wherein the upper rear panel is formed of material which stretches in both the horizontal and vertical directions and the middle rear panel is formed of material which stretches in the horizontal direction but is substantially inelastic in the vertical direction.

2. An ankle brace, comprising:
   (a) a base of flexible material shaped to wrap around the sides of a foot and ankle and underneath a portion of the foot, the base having first and second sides each having a forward edge, and a sole portion having inside and outside surfaces and forward and rear edges;
   (b) an elongate sole member having a first end fixed adjacent to the forward edge of the sole portion of the base and a second end fixed adjacent to the rear edge of the sole portion of the base, wherein the elongate sole member is not otherwise fixed to the base; and
   (c) a support strap having a first end fixed to the base adjacent to the forward edge of the first side of the base and a second end fixed to the base adjacent to the forward edge of the second side of the base wherein the support strap is not otherwise fixed to the sole portion of the base, wherein the support strap is not fixed to the elongate sole member, and wherein the support strap extends between the elongate sole member and the inside surface of the sole portion of the base.

3. The ankle brace of claim 2 wherein the first and second sides of the base each have a rear edge and the rear edges of the first and second sides each have an upper portion and a middle portion, and further comprising an upper rear panel having a first end fixed to the upper portion of the rear edge of the first side of the base and a second end fixed to the upper portion of the rear edge of the second side of the base.

4. The ankle brace of claim 3 wherein the upper rear panel is formed of material which stretches in both the horizontal and vertical directions.

5. The ankle brace of claim 3 further comprising a middle rear panel having a first end fixed to the middle portion of the rear edge of the first side of the base and a second end fixed to the middle portion of the rear edge of the second side of the base.

6. The ankle brace of claim 5 wherein the upper rear panel is formed of material which stretches in both the horizontal and vertical directions.

7. The ankle brace of claim 5 wherein the upper rear panel is formed of material which stretches in both the horizontal and vertical directions and the middle rear panel is formed of material which stretches in the horizontal direction but is substantially inelastic in the vertical direction.

8. An ankle brace, comprising:
(a) a base of flexible material shaped to wrap around the sides of a foot and ankle and underneath a portion of the foot, the base having first and second sides each having a forward edge, and a sole portion having inside and outside surfaces and forward and rear edges;
(b) at least one elongate pocket on at least one side of the base, and at least one resilient stay member located in an elongate pocket;
(c) an elongate sole member having a first end fixed adjacent to the forward edge of the sole portion of the base and a second end fixed adjacent to the rear edge of the sole portion of the base wherein the elongate sole member is not otherwise fixed to the base; and
(d) a support strap having a first end fixed to the base adjacent to the forward edge of the first side of the base and a second end fixed to the base adjacent to the forward edge of the second side of the base wherein the support strap is not otherwise fixed to the sole portion of the base, wherein the support strap is not fixed to the elongate sole member, and wherein the support strap extends between the elongate sole member and the inside surface of the sole portion of the base.

9. The ankle brace of claim 8 wherein the first and second sides of the base each have a rear edge and the rear edges of the first and second sides each have an upper portion and a middle portion, and further comprising an upper rear panel having a first end fixed to the upper portion of the rear edge of the first side of the base and a second end fixed to the upper portion of the rear edge of the second side of the base.

10. The ankle brace of claim 9 wherein the upper rear panel is formed of material which stretches in both the horizontal and vertical directions.

11. The ankle brace of claim 9 further comprising a middle rear panel having a first end fixed to the middle portion of the rear edge of the first side of the base and a second end fixed to the middle portion of the rear edge of the second side of the base.

12. The ankle brace of claim 11 wherein the upper rear panel is formed of material which stretches in both the horizontal and vertical directions.

13. The ankle brace of claim 11 wherein the upper rear panel is formed of material which stretches in both the horizontal and vertical directions and the middle rear panel is formed of material which stretches in the horizontal direction but is substantially inelastic in the vertical direction.

14. An ankle brace, comprising:
(a) a base of flexible material shaped to wrap around the sides of a foot and ankle and underneath a portion of the foot, the base having first and second sides each having a forward edge, and a sole portion having inside and outside surfaces and forward and rear edges;
(b) a support strap having a first end detachably attachable to the base adjacent to the forward edge of the first side of the base and a second end detachably attachable to the base adjacent to the forward edge of the second side of the base wherein the support strap is not otherwise fixed to the sole portion of the base; and
(c) an elongate sole member having a first end detachably attachable adjacent to the forward edge of the sole portion of the base and a second end detachably attachable adjacent to the rear edge of the sole portion of the base, wherein the elongate sole member is not otherwise fixed to the base, the support strap is not fixed to the elongate sole member, and the support strap extends between the elongate sole member and the inside surface of the sole portion of the base.

15. An ankle brace, comprising:
(a) a base of flexible material shaped to wrap around the sides of a foot and ankle and underneath a portion of the foot, the base having first and second sides each having a forward edge, and a sole portion having inside and outside surfaces and forward and rear edges; and
(b) a support strap having a first end detachably attachable to the base adjacent to the forward edge of the first side of the base and a second end detachably attachable to the base adjacent to the forward edge of the second side of the base wherein the support strap is not otherwise fixed to the sole portion of the base;
wherein the first and second sides of the base each have a rear edge and the rear edges of the first and second sides each have an upper portion and a middle portion, and further comprising an upper rear panel having a first end fixed to the upper portion of the rear edge of the first side of the base and a second end fixed to the upper portion of the rear edge of the second side of the base; and
further comprising a middle rear panel having a first end fixed to the middle portion of the rear edge of the first side of the base and a second end fixed to the middle portion of the rear edge of the second side of the base;
wherein the upper rear panel is formed of material which stretches in both the horizontal and vertical directions and the middle rear panel is formed of material which stretches in the horizontal direction but is substantially inelastic in the vertical direction.

* * * * *